(12) United States Patent
Horvath

(10) Patent No.: US 12,285,535 B2
(45) Date of Patent: Apr. 29, 2025

(54) CHLORINE DIOXIDE GENERATING DEVICE

(71) Applicant: Kenneth Horvath, Prescott, AZ (US)

(72) Inventor: Kenneth Horvath, Prescott, AZ (US)

( * ) Notice: Subject to any disclaimer, the term of this patent is extended or adjusted under 35 U.S.C. 154(b) by 214 days.

(21) Appl. No.: 16/595,145

(22) Filed: Oct. 7, 2019

(65) Prior Publication Data
US 2020/0038536 A1     Feb. 6, 2020

Related U.S. Application Data

(63) Continuation of application No. 15/612,948, filed on Jun. 2, 2017, now abandoned.

(51) Int. Cl.
| A61L 2/26 | (2006.01) |
| A01M 1/20 | (2006.01) |
| A01M 13/00 | (2006.01) |
| A61L 2/20 | (2006.01) |
| A61L 9/04 | (2006.01) |
| A61L 9/12 | (2006.01) |
| C01B 11/02 | (2006.01) |
| A61L 2/18 | (2006.01) |

(52) U.S. Cl.
CPC .............. *A61L 2/26* (2013.01); *A01M 1/2033* (2013.01); *A01M 13/00* (2013.01); *A61L 2/20* (2013.01); *A61L 9/046* (2013.01); *A61L 9/12* (2013.01); *A61L 9/122* (2013.01); *C01B 11/022* (2013.01); *A61L 2/18* (2013.01); *A61L 2202/11* (2013.01); *A61L 2202/15* (2013.01); *A61L 2209/134* (2013.01); *A61L 2209/21* (2013.01)

(58) Field of Classification Search
CPC ..... A61L 2/26; A61L 2/24; A61L 2/20; A61L 2/23; A61L 9/046; A61L 9/12; A61L 9/122; A61L 2209/134; A61L 2209/21; A01M 1/2033; A01M 13/00
See application file for complete search history.

(56) References Cited

U.S. PATENT DOCUMENTS

| 3,035,421 | A | * | 5/1962 | Halbeisen | ............. | F24F 13/075 |
| | | | | | | 62/426 |
| 4,099,747 | A | * | 7/1978 | Meserole | ............. | F16L 37/084 |
| | | | | | | 285/148.15 |
| 4,583,686 | A | | 4/1986 | Martens et al. | | |
| 5,328,646 | A | * | 7/1994 | Bryson | ................... | F24F 3/12 |
| | | | | | | 261/52 |
| 6,363,734 | B1 | | 4/2002 | Aoyagi | | |
| 7,871,016 | B2 | * | 1/2011 | Ricciardi | ................. | A61L 2/22 |
| | | | | | | 239/67 |

* cited by examiner

*Primary Examiner* — Timothy C Cleveland
(74) *Attorney, Agent, or Firm* — Zeman-Mullen & Ford, LLP

(57) ABSTRACT

A device for generating and dispersing chlorine dioxide which includes a housing, at least one removeable tray having a plurality of compartments contained within an interior of the housing, and a fan in communication with the interior of the housing and the exterior of the housing for directing a current of chlorine dioxide gas that is generated from chemicals that are positioned within the removeable tray(s).

12 Claims, 6 Drawing Sheets

CHLORINE DIOXIDE GENERATING DEVICE

CROSS-REFERENCE TO RELATED APPLICATIONS

This application is a continuation of and claims the benefit of, and priority to U.S. Nonprovisional patent application Ser. No. 15/612,948 filed Jun. 2, 2017, currently pending, which application is hereby incorporated by reference in its entirety.

FIELD OF INVENTION

The present invention generally relates to a chlorine dioxide generating and dispersing apparatus for using chlorine dioxide as an oxidizer or disinfectant for treating and/or eliminating smoke odors, mold, viruses, bacteria, fungi, and other pathogenic microorganisms, as well as pests such as insects and rodents that are destructive and/or carry disease. The chlorine dioxide generating apparatus includes a housing, at least one tray having a plurality of compartments that can be retained within the housing, and a fan in communication with the interior of the housing that is capable of directing a current of chlorine dioxide gas generated from chemicals that are positioned within the tray(s) contained within the housing.

BACKGROUND OF THE INVENTION

Chlorine dioxide ($ClO_2$) is a yellowish-green gas with a chlorine like, irritating odor. It is explosive under pressure and is difficult to transport. Therefore, when used, it is usually manufactured on site. Chlorine dioxide is usually produced as a watery solution or gas in acidic solutions of sodium chlorite ($NaClO_2$) or sodium chlorate ($NaClO_3$). An important quality of chlorine dioxide is its high water solubility, especially in cold water. The best way to store chlorine dioxide is as a liquid at 4 degrees Centigrade in that it is fairly stable at this state. Chlorine dioxide slowly dissociates into chlorine and oxygen and therefore cannot be stored for too long.

Chlorine dioxide can be used as an oxidizer or disinfectant. It is a very strong oxidizer and can effectively kill pathogenic microorganisms such as fungi, bacteria, and viruses. It can also prevent and remove bio film. Chlorine dioxide is very selective as an oxidizer and has a unique one-electron exchange mechanism. Chlorine dioxide attacks electron-rich centers of organic molecules where one electron is transferred and chlorine dioxide is reduced to chlorite. Compared to other disinfectants, chlorine dioxide is effective at low concentrations. For example, in comparison to chlorine and ozone, less chlorine dioxide is required to obtain an active residual disinfectant and the contact time to kill microorganisms is also very low. Chlorine dioxide also produces fewer disinfection byproducts than oxidators such as chlorine and disinfection with chlorine dioxide does not cause odor nuisance.

Although chlorine dioxide is an effective oxidizer and disinfectant, the time required to set up large areas for treatment can expose a user to dangerous conditions and injuries, especially when disinfection takes place in sealed areas. When chlorine dioxide concentrations reach 10% or more in air, chlorine dioxide becomes explosive. In addition, chlorine dioxide can be absorbed by the skin where it damages tissue and blood cells. Exposure of one's eyes to chlorine dioxide causes irritation, watering eyes, and blurry sight and inhalation of chlorine dioxide gas can cause coughing, a sore throat, severe headaches, lung oedema, and bronchial spasms. These symptoms can begin long after the exposure has taken place and can remain for a long time.

Accordingly, there is a need for an apparatus that provides efficient and effective generation and dispersement of chlorine dioxide for oxidizing and/or disinfecting different sized areas while minimizing exposure of chlorine dioxide to an operator of the apparatus. There is also a need for an apparatus that generates chlorine dioxide that enables a user to efficiently and effectively utilize both the chlorine dioxide gas and the chlorine dioxide liquid that are generated from the apparatus.

SUMMARY OF THE INVENTION

The present invention is directed to a device for generating and dispersing chlorine dioxide gas for use as an oxidizer or disinfectant within different sized areas for treating and/or eliminating odors, mold, mildew, viruses, bacteria, fungi, and other pathogenic microorganisms, as well as pests such as insects and rodents that are destructive and/or carry disease. The chlorine dioxide generating device can be used within different sized areas, from small areas to large areas, and ducting may be attached to the device to more precisely direct the dispersal of chlorine dioxide generated by the device.

In one exemplary embodiment, the chlorine dioxide generating device includes a housing, at least one removeable tray having a plurality of compartments contained within an interior of the housing, and a fan in communication with the interior of the housing and the exterior of the housing for directing a current of chlorine dioxide gas that is generated from chemicals that are positioned within the removeable tray(s). The housing may further include an opening located opposite the fan for enabling air to be drawn into the interior of the housing. At least a portion of the housing may be moveable or removeable to enable the tray(s) to be removed from the interior of the housing. One exemplary embodiment of the moveable portion of the housing may take the form of a door contained within the housing that opens to provide access to the interior of the housing. The door may be located at any position on the housing such as the back, sides, or top of the housing in order to gain access to an interior of the housing.

The one or more removeable trays having a plurality of compartments may also include a handle for easy insertion and removal of the trays into the interior of the housing. The one or more removable trays may also each have a lid to make the trays spillproof when transporting the trays containing chemicals and/or liquids. The one or more removeable trays may also include an open area that is separate from the plurality of compartments and larger than each individual compartment. This open area enables for easy pouring of chlorine dioxide liquid from the tray after treatment with the device so that the chlorine dioxide liquid can be poured into a container or other vessel and used for further disinfecting or other purposes.

The fan may be positioned at an upward angle relative to a bottom and/or side of the housing to aid in properly circulating the chlorine dioxide gas throughout the treatment area. The fan may lie adjacent to an opening in the housing through which a current generated by the fan is directed. Air may be drawn into one or more openings in the housing located opposite the fan to create a slight negative pressure within the housing so that chlorine dioxide gas generated form the chemicals and/or liquids in the removeable tray(s)

will exit through the fan. The opening in the housing through which chlorine dioxide gas is dispersed by the fan may include an indentation that can function as a pour spout for liquid that may be retained within an interior of the housing from spills that have occurred during use of the device. This same opening may take a shape that enables ducting to be attached to the opening on order to more precisely direct the flow of chlorine dioxide gas exiting the fan.

BRIEF DESCRIPTION OF THE DRAWINGS

The subject invention will hereinafter be described in conjunction with the appended drawing figures, wherein like numerals denote like elements.

DESCRIPTION OF EXEMPLARY EMBODIMENTS

Figure 1:
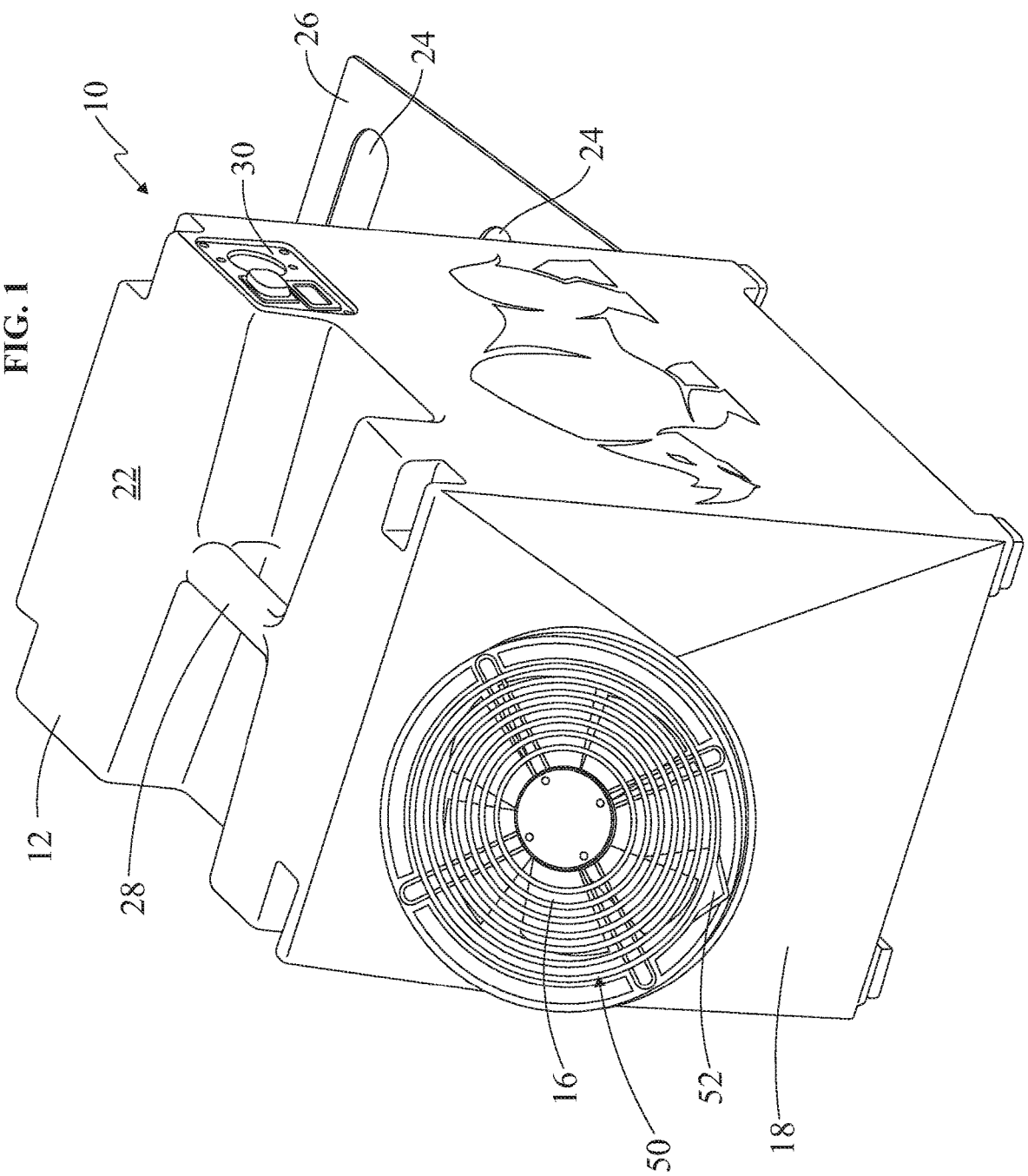
FIG. 1 is a front perspective view of an exemplary embodiment of the chlorine dioxide generating device of the present invention.

The device 10 for generating and dispersing chlorine dioxide gas of the present invention generally provides a housing 12, at least one removeable tray 14 (See FIGS. 2 and 3) having a plurality of compartments contained within an interior of the housing 12, and a fan 16 in communication with the interior of the housing 12 and the exterior of the housing 12 for directing a current of chlorine dioxide gas that is generated from chemicals that are positioned. within the removeable tray(s) 14. Housing 12 may have a front 18, back 20, top 22, and bottom (not shown). Housing 12 also includes an interior chamber for retaining removable trays 14 and fan 16.

Figure 2:
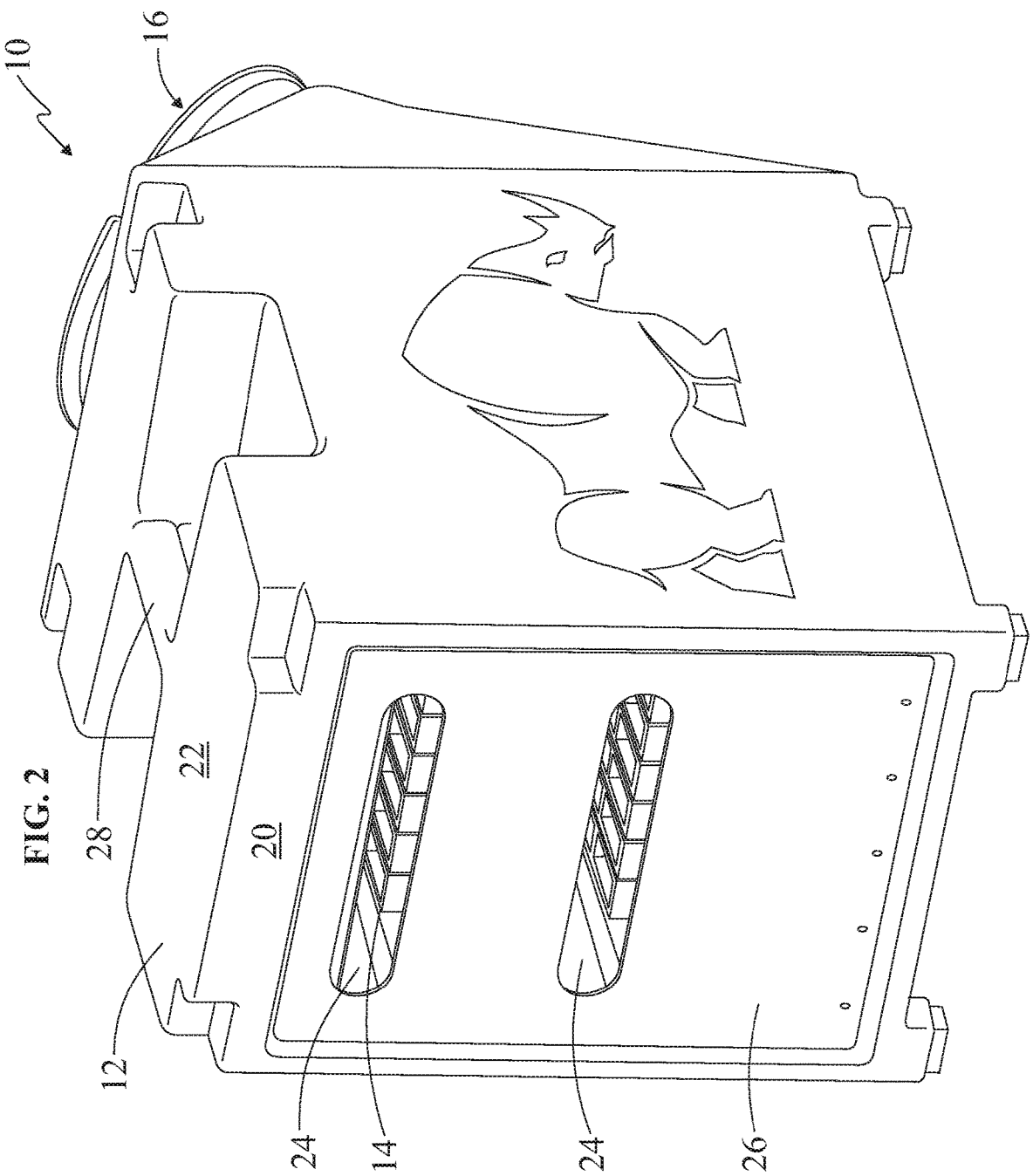
FIG. 2 is a rear perspective view of the exemplary embodiment of the chlorine dioxide generating device of the present invention shown in FIG. 1.
Figure 3:
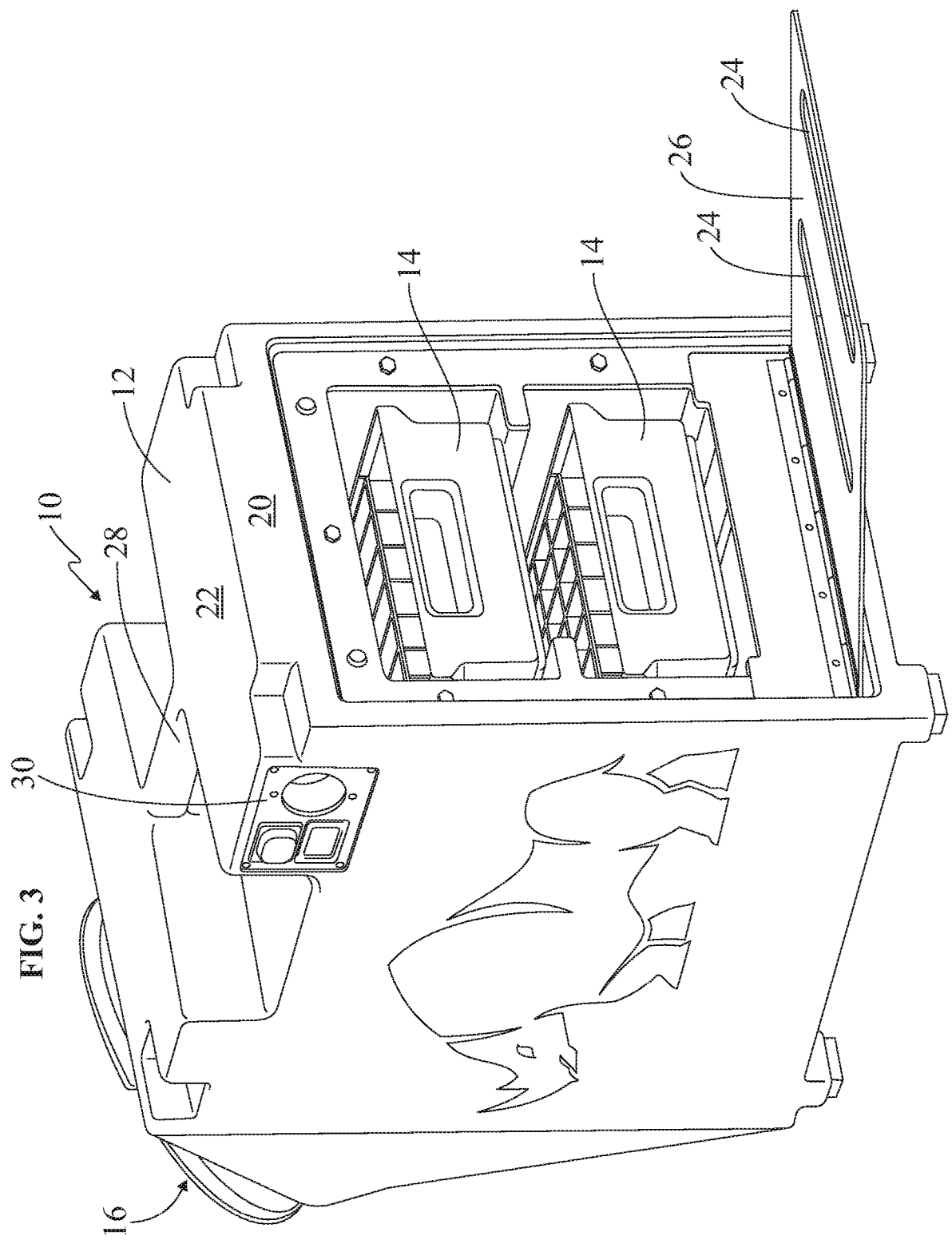
FIG. 3 is a another rear perspective view of the exemplary embodiment of the chlorine dioxide generating device of the present invention depicted in FIG. 1 showing a door located on the rear of the housing in an open position.

The back 18 of housing 12 includes at least one opening 24 for enabling air to be drawn into the interior of the housing 12 and over removable trays 14. At least a portion of the back 18 of housing 12 is moveable or removeable to enable access into the interior of the housing 12 so that the removeable trays 14 can be inserted into and removed from the interior of housing 12. The moveable or removeable portion of housing 12 takes the form of a door 26 as shown in FIGS. 1-3. The door 26 may be located at other positions on the housing such as the sides or top of the housing 12 in order to gain access to an interior of the housing 12.

Housing 12 may be comprised of any strong and durable material such as, for example, a polymer or a metal. Door 26 may also be comprised of a polymer or a metal but may preferably be comprised of a stainless steel to resist corrosion that could result from the increased exposure to chlorine dioxide to that portion of the housing 12. Device 10 may also include a handle 28 on the top 22 of housing 12. Handle 28 may be integral with and formed as part of top 22 of housing 12 or may be separate from top 22 of housing 12.

Device 10 also includes control panel 30 for operating/activating the device 10. Control panel 30 may also include a display showing the amount of time device 10 has been operating and/or a measurement of the concentration of chlorine dioxide in the air immediately surrounding the device 10. Device 10 may be powered by batteries and/or an electrical cord that plugs into a power source.

Figure 4:
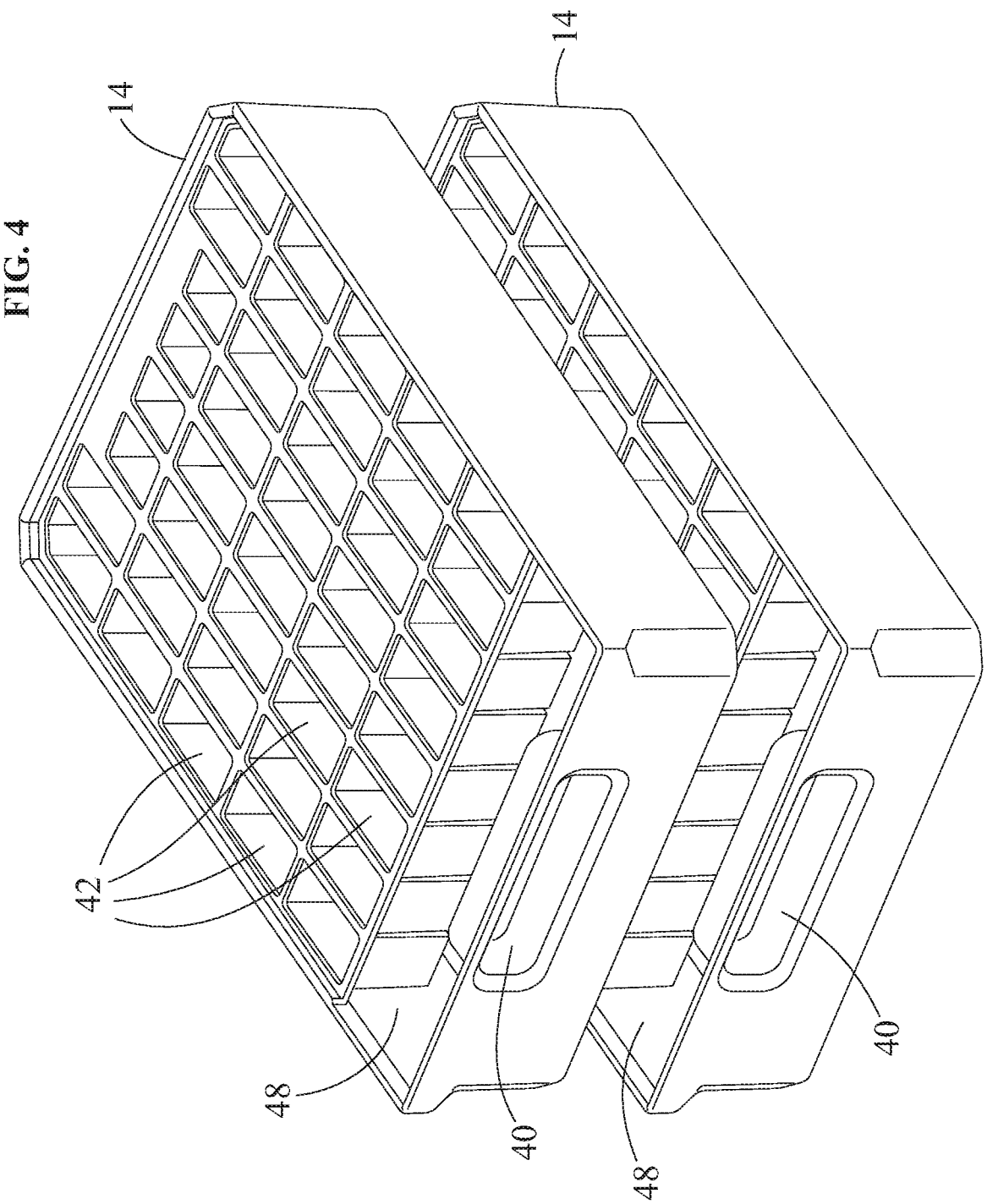
FIG. 4 is a top perspective view of an exemplary embodiment of the removeable trays contained within the exemplary embodiment of the chlorine dioxide generating device of the present invention shown in FIG. 1.
Figure 5:
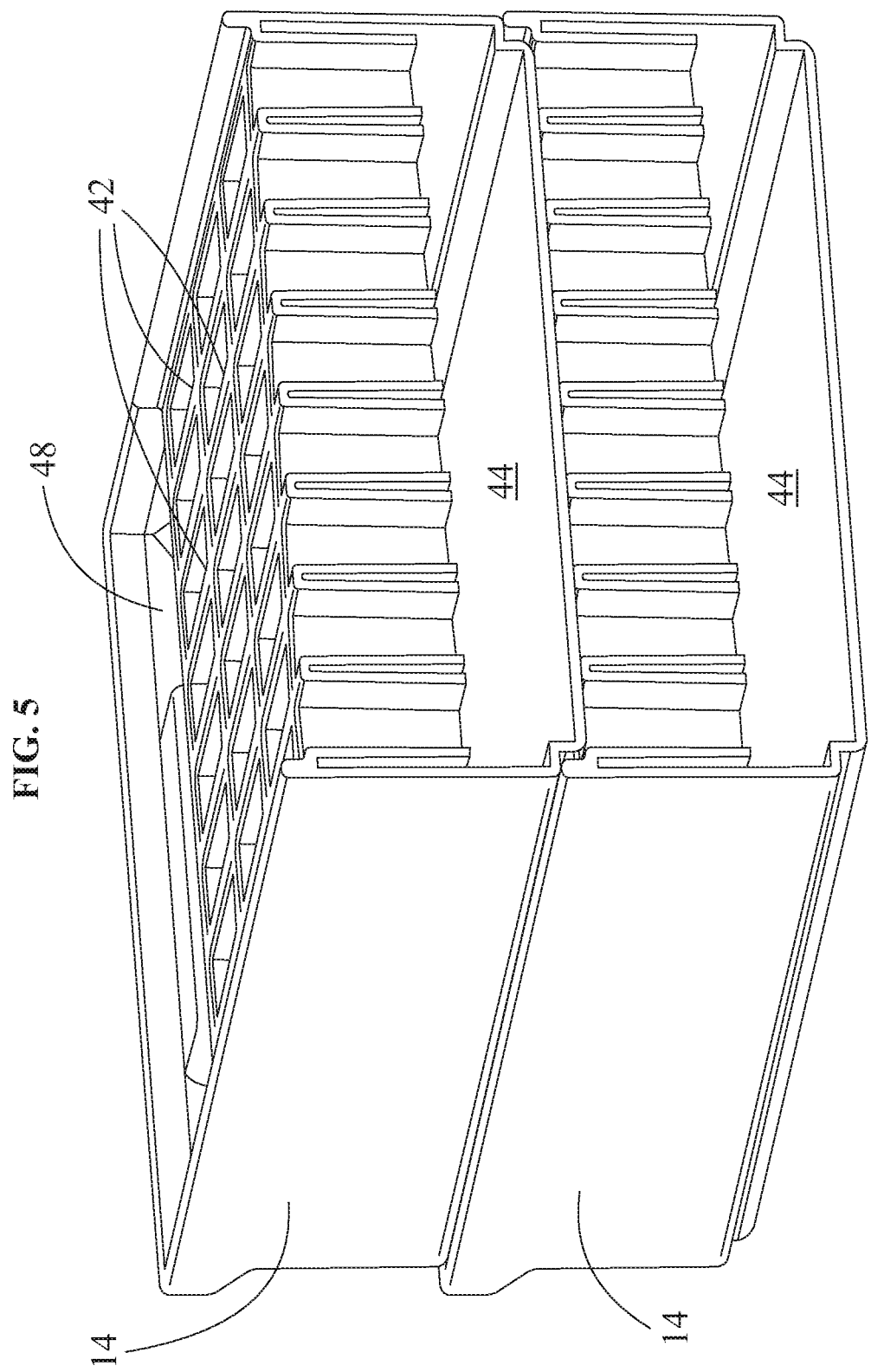
FIG. 5 is a rear perspective view of the exemplary embodiment of the removeable trays shown in FIG. 4 with the back ends of the trays removed to show the plurality of compartments contained within the trays.

Perspective views of an exemplary embodiment of removeable trays 14 are shown in FIGS. 4 and 5. Removeable trays 14 may be stackable and may also have lids to avoid spills while transporting the trays when they contain chemicals and/or liquids. Removeable trays 14 may have a handle 40 to assist in inserting and removing the trays 14 from the interior of the housing 12. Removeable trays 14 each include a plurality of compartments 42 which function to hold packets or tablets comprising chemicals such as sodium chlorite or similar chemicals that are used to produce chlorine dioxide.

In the exemplary embodiment of the removeable trays 14 shown in FIGS. 4 and 5, each of the plurality of compartments 42 have an open top and an open bottom where the bottom of the compartments 42 are positioned above the bottom 44 of the trays 14 thereby providing a space between the bottom of the compartments 42 and the bottom 44 of the trays 14. This exemplary embodiment of the removeable trays 14 are used when packets of chemicals are used to produce the chlorine dioxide. The packets containing the chemicals fit in separate compartments 42, one packet for each compartment 42, and the each packet extends to the bottom 44 of the trays 14. Once the packets are loaded into the compartments 42, water is the poured into the trays 14. The water wicks up each packet and activates the chemicals inside the packet to produce the chlorine dioxide. When the device 10 is activated/turned on, the opening(s) 24 in the back 20 of housing 12 and the fan 16 at the front 18 of housing 12 cause chlorine dioxide gas to be drawn from the trays 14 to the fan 16 so that the chlorine dioxide gas exits the interior chamber of the housing 12 through the front of the fan 16. Since the trays 14 can be preloaded with packets and then filled all at once with water, this minimizes the user's exposure to the chlorine dioxide gas.

The trays 14 allow for the off gassing of chlorine dioxide as previously mentioned but also function to retain chlorine dioxide liquid that results from mixing the packets of chemicals with water. Removeable trays 14 also have an open area 48 that is separate from the plurality of compartments 42, and larger than each of the individual compartments 42. The chlorine dioxide liquid that is produced and retained within the trays 14 can then be poured from this open area 48 of the trays 14 into a container or other vessel so that it can be used to spray, roll, and/or wipe on a surface for disinfecting the surface, removing odors, and/or killing and eliminating pathogens. The device of the present invention enables a user of the device to efficiently and effectively utilize both the chlorine dioxide gas and the chlorine dioxide liquid that are produced from combining the chemical packets and water.

In another exemplary embodiment, the removeable trays 14 have a plurality of compartments that each have an open top and a closed bottom that lies adjacent to the bottom 44 of the trays 14. Alternatively, the plurality of compartments may each have an open top and an open bottom but the open bottom fits against the bottom 44 of trays 14 so that the plurality of compartments are completely separate from one another and there is no avenue of communication between the compartments. This embodiment of the trays 14 is used when tablets of chemicals are used to create the chlorine dioxide. Tablets of chemicals are seated within each individual compartment and water is poured into all of the compartments. When the device 10 is activated/turned on, the opening(s) 24 in the back 20 of housing 12 and the fan 16 at the front 18 of housing 12 cause chlorine dioxide gas to be drawn from the trays 14 to the fan 16 so that the chlorine dioxide gas exits the interior chamber of the housing 12 through the front of the fan 16. Since the trays 14 can be preloaded with tablets and then filled all at once with water, this minimizes the user's exposure to the chlorine dioxide gas. With this embodiment of the trays, chlorine dioxide liquid would be retained within the bottom of each separate compartment and would not collect in the bottom of the tray 14 like the embodiment of the trays 14 shown in FIGS. 4 and 5.

Figure 7:
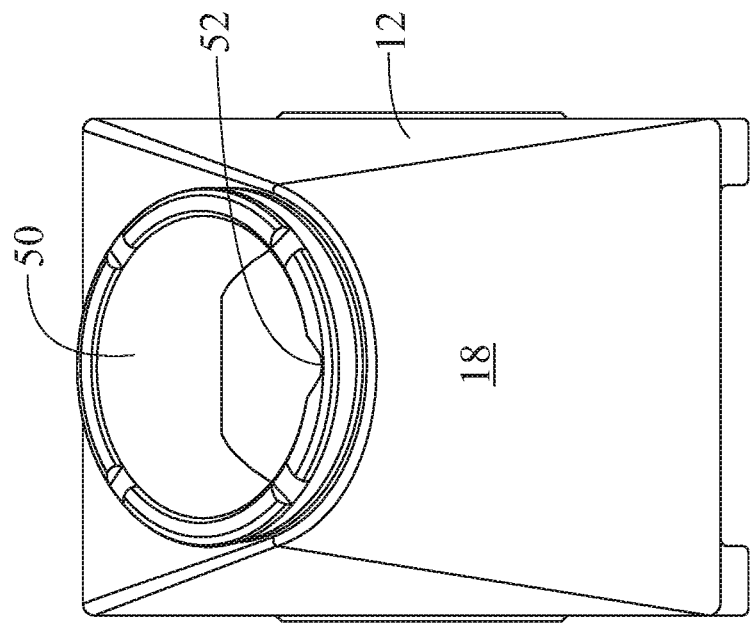
FIG. 7 is a front view of the exemplary embodiment of the chlorine dioxide generating device of the present invention depicted in FIG. 1 shown without the fan contained within the housing.
Figure 6:
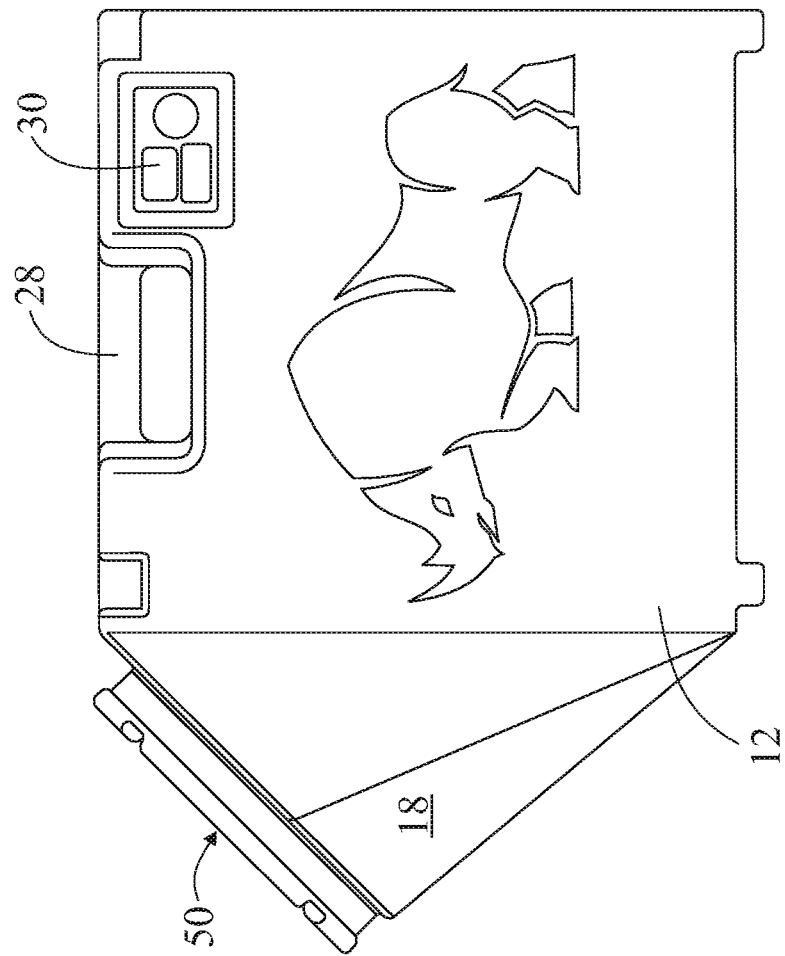
FIG. 6 is a side view of the exemplary embodiment of the chlorine dioxide generating device of the present invention shown in FIG. 1.

As previously described above, fan 16 is seated within an interior chamber of housing 12 but is exposed to the exterior of housing 12 through an opening 50 located in the front 18 of housing 12 and opposite the opening(s) 26 in the back 20 of housing 12. This enables air to be drawn into the interior of the opening(s) 26 and chlorine dioxide gas generated from trays 14 is drawn from the trays 14 to the fan 16 so that it exits the fan 16 through the opening 50 in the front 18 of housing 12. The opening 50 is shown as a circular opening in FIGS. 1 and 7 and a tubular shaped ducting can be connected to the circular opening 50 to more precisely direct the flow of chlorine dioxide gas exiting the fan. This is sometimes useful when the treatment area is within a crawl space or other hard to access area. Opening 50 also includes an indentation 52 that functions as a pour spout for pouring any spilled liquid, including chlorine dioxide liquid, from the housing. Further, as shown in FIGS. 1 and 6-7, circular opening 50 can have a size at least one third as large as the size of the front 18 of the housing 12.

The fan 16 is angled upward relative to the bottom and/or front of the device 10. Since chlorine dioxide gas is heavier than air, the fan 16 and the upward angle of the fan 16 control where the gas is dispersed and ensure that the gas is properly circulated through the treatment area. Fan 16 is preferably comprised of a corrosive resistant material.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and a equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A device for use with chemicals to generate chlorine dioxide into an unoccupied treatment area comprising:
   a housing having a top, a bottom, a front having a circular shaped opening therein facing upward relative to the bottom of the housing, and a back;
   at least one tray having a plurality of compartments contained therein capable of retaining one or more chemicals for generating chlorine dioxide wherein the tray is capable of being retained within an interior of the housing; and
   a circular fan having nearly a same diameter as the circular opening in the front of the housing wherein the circular fan is positioned within the interior of the housing immediately next to the circular opening in the front of the housing such that an entire front of the circular fan sits within the circular opening and treated air within the housing is dispensed through the fan and out of the housing into the unoccupied treatment area at an upward angle relative to the front of the housing.

2. The device of claim 1 wherein the back of the housing includes at least one opening therethrough for enabling air to be drawn into the interior of the housing.

3. The device of claim 1 wherein at least a portion of the back of the housing is moveable to enable access into the interior of the housing.

4. The device of claim 3 wherein the moveable portion of the back of the housing comprises a door.

5. The device of claim 1 wherein the plurality of compartments in said at least one tray are suspended above a bottom of the tray and each of the plurality of compartments have an open top and an open bottom.

6. The device of claim 5 wherein said at least one tray includes an open area that is separate from the plurality of compartments and larger than each individual compartment.

7. The device of claim 1 wherein the circular opening in the front of the housing includes a single indentation that can function as a pour spout that allows for directed flow of liquid from an interior of the housing.

8. A device for use with chemicals to generate chlorine dioxide into a treatment area comprising:
   a housing having a top, a bottom, a front, a back, and a single interior chamber located between the front and the back wherein components contained within the single interior chamber consist of:
      at least one tray having a plurality of compartments contained therein capable of retaining one or more chemicals for generating chlorine dioxide wherein the tray is capable of being retained within the single interior chamber of the housing; and a fan wherein an entire front of the fan fits within an opening in the front of the housing such that it is positioned at an upward angle relative to the front of the housing so that treated air within the housing is dispensed through the fan and out of the housing into the treatment area at an upward angle relative to the front of the housing.

9. The device of claim 8 wherein the back of the housing includes at least one opening therethrough for enabling air to be drawn into the interior of the housing.

10. The device of claim 8 wherein at least a portion of the back of the housing is moveable to enable access into the interior of the housing.

11. The device of claim 8 wherein the opening in the front of the housing includes a single indentation that can function as a pour spout that allows for directed flow of liquid from the single interior chamber.

12. The device of claim 8 further comprising a control panel which displays a measurement of chlorine dioxide concentration in the air immediately surrounding the device.

* * * * *